US007585662B2

(12) United States Patent
Weiblen et al.

(10) Patent No.: US 7,585,662 B2
(45) Date of Patent: Sep. 8, 2009

(54) CONTAINER FOR AN ANALYSIS CHIP

(75) Inventors: Kurt Weiblen, Metzingen (DE); Hubert Benzel, Pliezhausen (DE)

(73) Assignee: Robert Bosch GmbH, Stuttgart (DE)

( * ) Notice: Subject to any disclaimer, the term of this patent is extended or adjusted under 35 U.S.C. 154(b) by 589 days.

(21) Appl. No.: 10/477,160

(22) PCT Filed: Mar. 27, 2002

(86) PCT No.: PCT/DE02/01110

§ 371 (c)(1),
(2), (4) Date: Apr. 29, 2004

(87) PCT Pub. No.: WO02/089985

PCT Pub. Date: Nov. 14, 2002

(65) Prior Publication Data

US 2004/0180425 A1 Sep. 16, 2004

(30) Foreign Application Priority Data

May 9, 2001 (DE) ................................ 101 22 457

(51) Int. Cl.
*C12M 1/34* (2006.01)
*C12M 3/00* (2006.01)
*C12Q 1/70* (2006.01)

(52) U.S. Cl. ........................................ 435/287.2; 435/6

(58) Field of Classification Search .............. 435/287.2, 435/6

See application file for complete search history.

(56) References Cited

U.S. PATENT DOCUMENTS

| | | | | |
|---|---|---|---|---|
| 3,655,515 | A | 4/1972 | Noorlander | |
| 5,484,731 | A * | 1/1996 | Stevens | 435/305.3 |
| 5,488,447 | A * | 1/1996 | Patton et al. | 396/578 |
| 5,945,334 | A | 8/1999 | Goss et al. | |
| 6,048,498 | A | 4/2000 | Kennedy | |
| 6,864,097 | B1 * | 3/2005 | Schembri et al. | 436/165 |

FOREIGN PATENT DOCUMENTS

| | | |
|---|---|---|
| EP | 0 627 358 | 12/1994 |
| JP | 00-227414 | 8/2000 |
| WO | WO 96 14933 | 5/1996 |
| WO | WO 99 43432 | 9/1999 |
| WO | WO 01/5505 | 1/2001 |

OTHER PUBLICATIONS

Translation of the JP Patent Publication 2000-227414 p. 1-10.*

* cited by examiner

*Primary Examiner*—Walter D Griffin
*Assistant Examiner*—Lydia Edwards
(74) *Attorney, Agent, or Firm*—Kenyon & Kenyon LLP

(57) ABSTRACT

A receptacle is provided for accommodating an analysis chip, which receptacle has openings in a housing having access to the analysis chip, which openings are protected from external influences by a movable protector, and for carrying out an analysis, a mechanism for moving the protector is provided such that an opening in the protector coincides with the receptacle openings.

11 Claims, 5 Drawing Sheets

Fig. 11
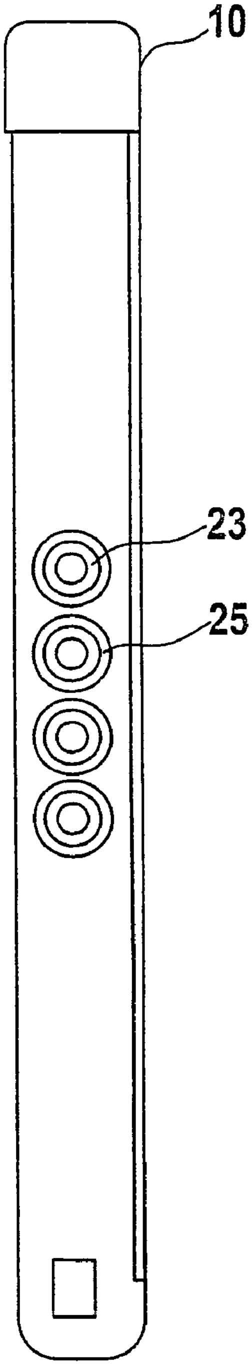
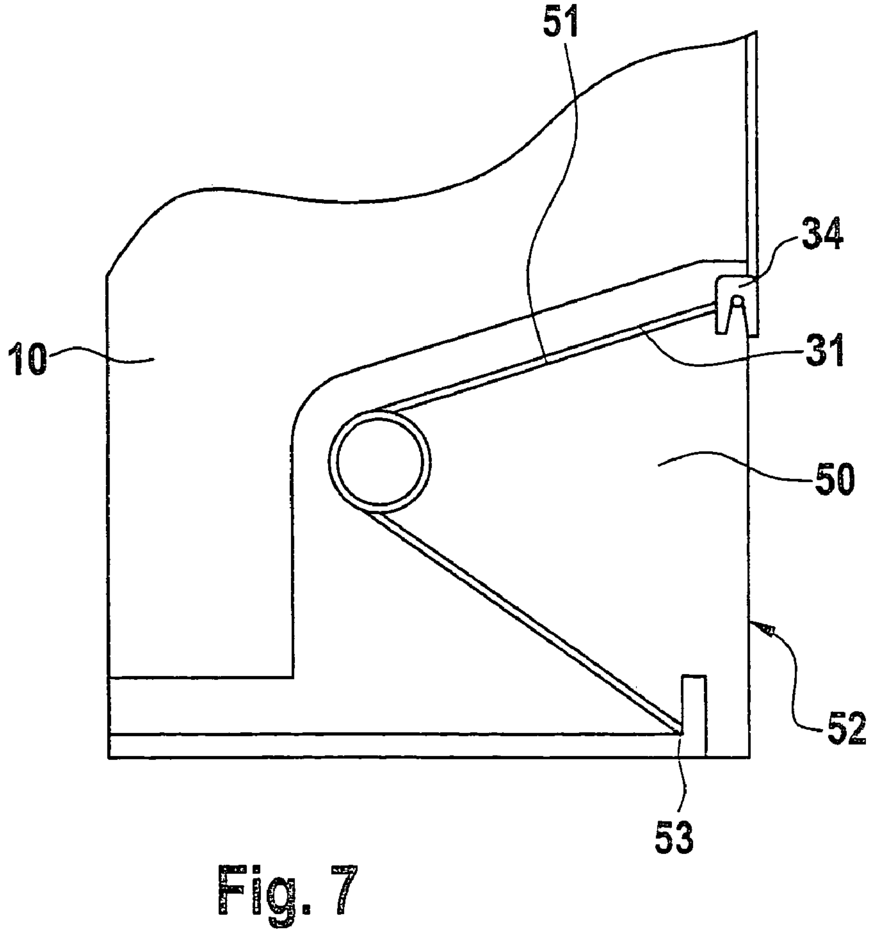
Fig. 7

Fig. 10
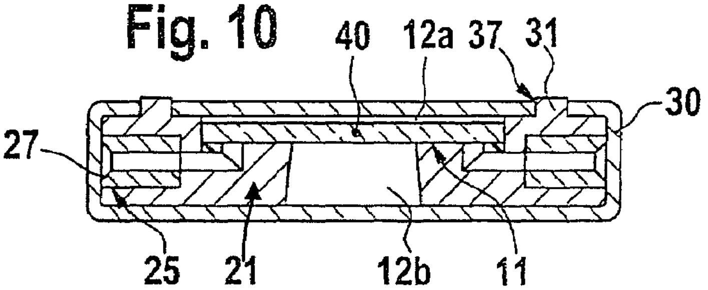
Fig. 9
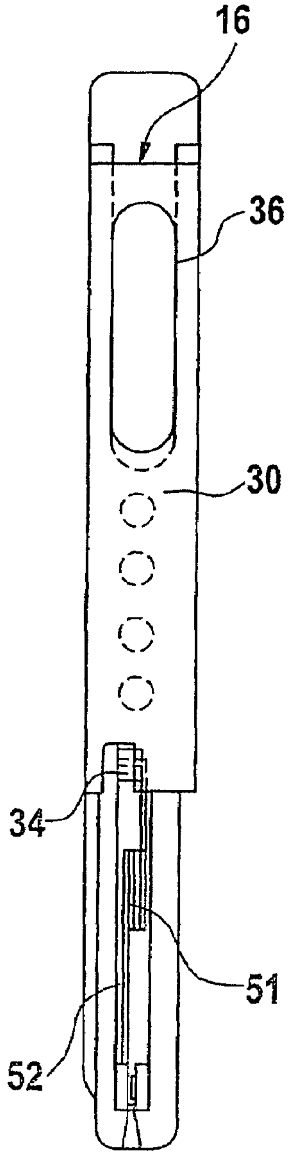
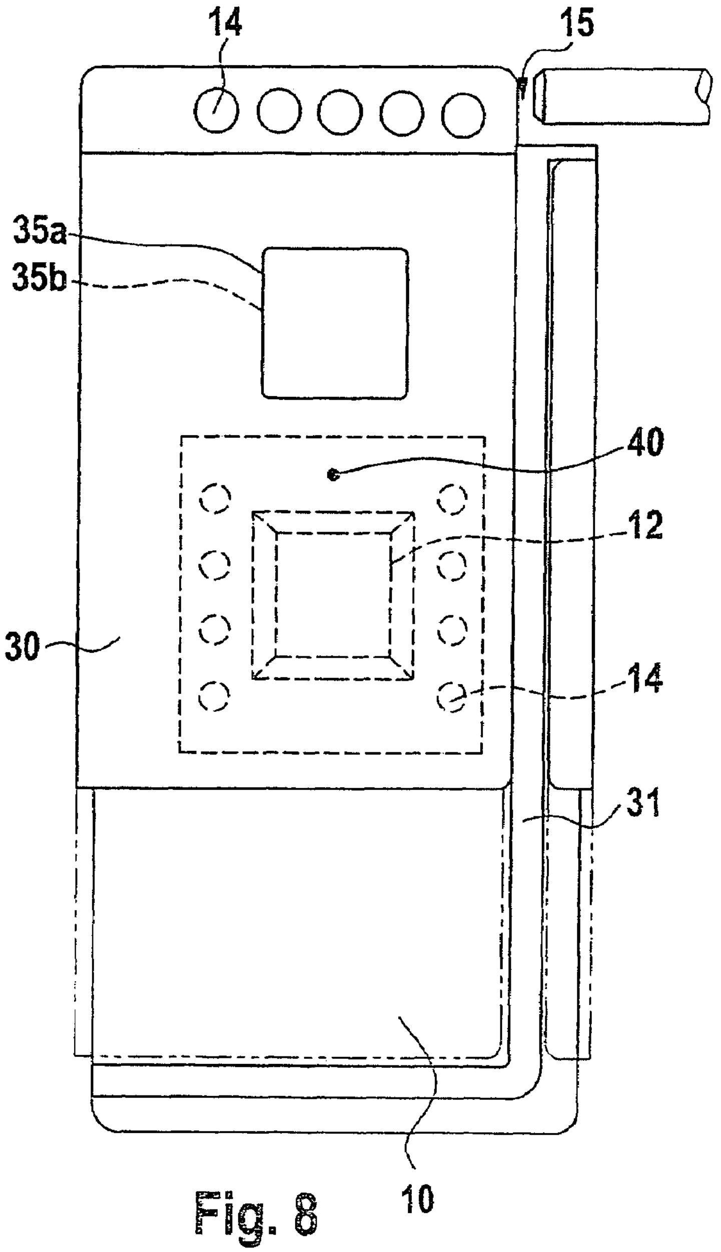
Fig. 8

Fig. 12
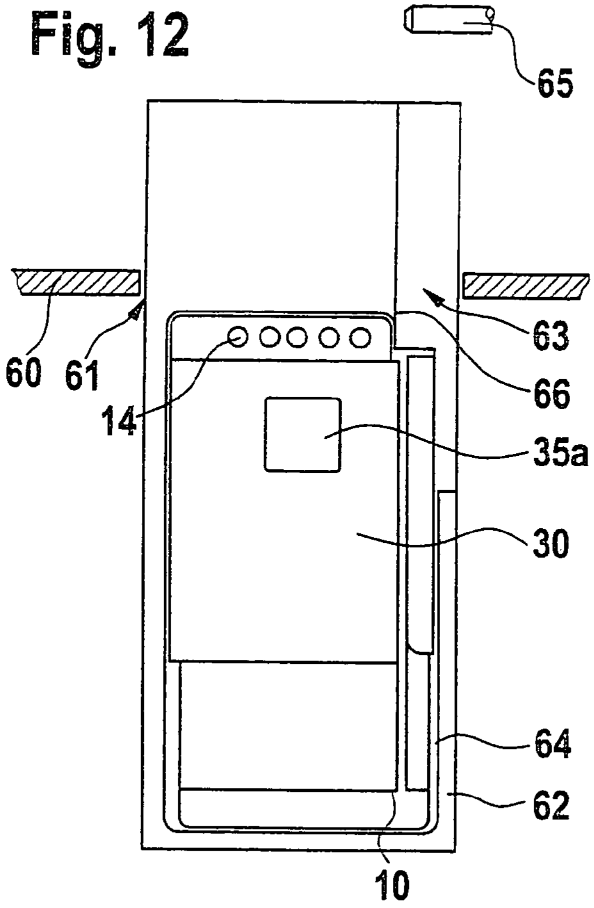
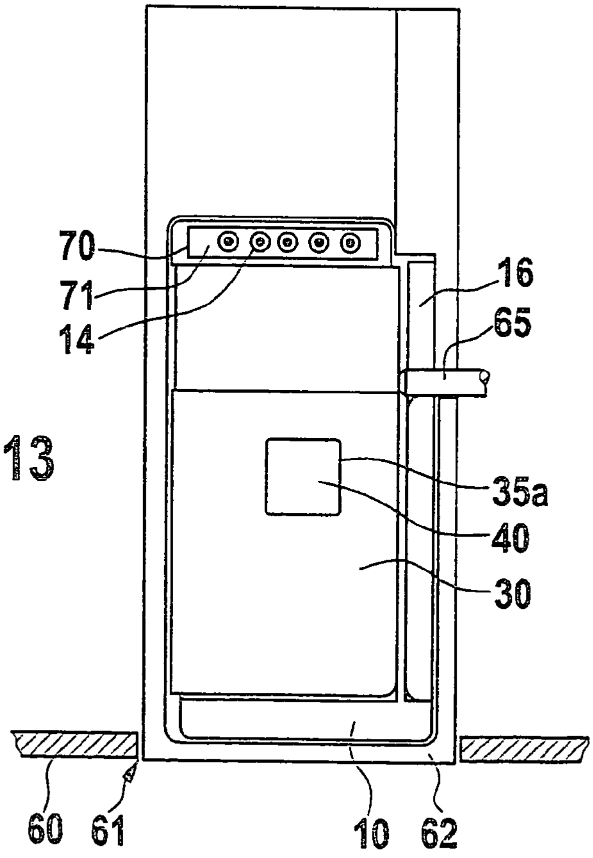
Fig. 13

CONTAINER FOR AN ANALYSIS CHIP

FIELD OF THE INVENTION

The present invention relates to a receptacle for accommodating an analysis chip, e.g., chip for the molecular analysis, and a device for accommodating such a receptacle.

BACKGROUND INFORMATION

Modern analysis, especially in the fields of medicine and biology, relies on increasingly compact analysis methods. In this connection, analysis chips are used, in the use of which the analysis steps are performed on the surface of an analysis chip. This surface mostly has a chemically active layer which, during the analysis procedure, is brought into contact with an analysis medium, a possible reaction of the analysis medium with the chip surface then being evaluated with the aid of suitable measuring methods. The analysis chip is able to have a densely packed array of fields which contain various chemical substances. Using this, then, permits a plurality of individual analyses on a single analysis chip.

The small-dimensioned chemically active structure of the analysis chip and the high requirements of carrying out an analysis process generally make the analysis chip very sensitive to external influences. Thus, even a slight contamination of the chip surface, such as a finger-print, is sufficient to make the analysis chip useless for rendering a meaningful analysis.

For this reason, analysis chips are manufactured and delivered under conditions of strict cleanliness. In particular, the analysis chips have to be carefully packed and protected from contamination, e.g., for transport and storage purposes. The analysis chips then have to be unpacked again for an analysis and brought into an analytical environment, the chip surface having to be reliably protected from contamination.

The above-named requirements for handling the analysis chips present a problem in practice, and make working with analysis chips rather difficult.

It is an object of the present invention to provide a cost-effective repackaging which will protect the sensitive chip surface from external influences and make possible the safe and simple handling of the analysis chip. It is a further object of the present invention to provide a device for the safe and simple handling of the repackaging along with the analysis chip.

SUMMARY

This object is attained by providing a receptacle according to the present invention, which has a housing including an accommodation for an analysis chip, into which the analysis chip is firmly installed, as well as access to an analysis medium, so that removing the analysis chip from the receptacle for the purpose of an analysis procedure is not necessary. This simplifies the handling of the analysis chip. The receptacle according to the present invention also has a movable protector, which, in a closed position, e.g., during a transport or storage procedure, covers the access for the analysis medium to the analysis chip which is present in the receptacle, and uncovers the access in an open position for the analysis medium during the analysis process. This reliably protects the access for the analysis medium, and consequently also the surface of the analysis chip, from external influences such as soiling.

According to one exemplary embodiment of the present invention, the receptacle has at least one additional opening area for checking the analysis chip, which opening is preferably designed as a window for an optical measuring method. This makes unnecessary the removal of the analysis chip from the receptacle for the purpose of evaluating the analytical process. In this context, the movable protector is designed in such a way that the additional opening area is also covered by a closing position of the protector. This avoids damage to the opening area by external influences, such as scratches, and with that, possible errors when reading out analysis results. Thereby, the meaningfulness of the analysis procedure is increased overall.

According to another exemplary embodiment of the present invention, the protector is a sliding protector which is slidingly supported along a guideway. This achieves an especially simple and easy-to-implement protective mechanism.

According to one further exemplary embodiment of the present invention, between the protector and the receptacle housing, the receptacle has a seal which may be made of a non-woven fabric. This ensures that the access of the receptacle to the analysis chip is also protected from small particles such as dust.

According to still another exemplary embodiment of the present invention, the receptacle housing has a coding region, which may be optically or mechanically scanned. This permits implementing a safety measure which prevents a mix-up of the analysis chips.

According to yet another exemplary embodiment of the present invention, the receptacle housing has a recess which clearly establishes the spatial orientation of the receptacle. This avoids that the analysis chip is put into the analysis device in a wrong way and thereby the entire analysis process is endangered.

The device for accommodating the receptacle according to the present invention has an accommodation region adapted to the receptacle, as well as a mechanism that brings the sliding protector of the receptacle from a closed position to an open position. The accommodating region, which may be designed as a drawer, makes possible simple and precise conveyance of the receptacle to an analysis device formed inside the device. The mechanism for opening the sliding protector of the receptacle, which may be designed as a pin, only uncovers the accesses to the analysis chip inside the device, so that these accesses, and consequently also the analysis chip itself, are protected from external influences which, for example, could have an effect on the analysis chip or its accesses, when the receptacle is mounted in the device with the sliding protector already open.

According to one exemplary embodiment of the present invention, for accommodating the receptacle according to the present invention, in the accommodating region of the device, a structural part may be designed in such a way that the structural part engages the recess on the receptacle housing. This ensures a clear position of the receptacle inside the accommodating device.

According to an additional exemplary embodiment of the device according to the present invention, for accommodating the receptacle according to the present invention, the device includes an optical or a mechanical scanning device for scanning the coding region designed to be on the receptacle housing. In this manner simple evaluation of the coding region of the receptacle is achieved, and consequently the risk of a mix-up with respect to the analysis chip used is clearly reduced.

BRIEF DESCRIPTION OF THE DRAWINGS

FIG. 7 shows an exemplary embodiment of a resetting mechanism for a sliding protector provided on a housing of the receptacle according to the present invention.

FIG. 8 shows a top view of an exemplary embodiment of a housing of the receptacle according to the present invention.

FIG. 9 shows a lateral view of the housing of the receptacle shown in FIG. 8.

FIG. 10 shows a cross-sectional view of the housing of the receptacle shown in FIG. 8, with an analysis chip having been set into a recess of the housing.

FIG. 11 shows another lateral view of the housing of the receptacle shown in FIG. 8, which has openings serving as connections for external supply lines and discharge lines.

FIG. 12 shows an exemplary embodiment for a device for accommodating the receptacle according to the present invention.

FIG. 13 shows the embodiment of FIG. 12 with the sliding protector in a different position.

DETAILED DESCRIPTION

Figure 1:
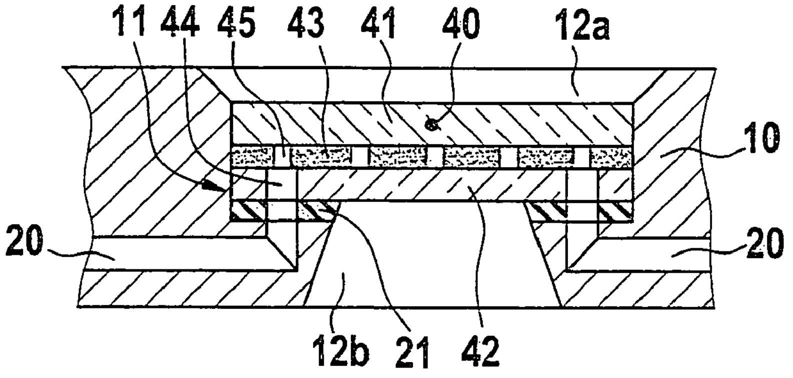
FIG. 1 shows details of an exemplary embodiment of a receptacle according to the present invention for accommodating analysis chips.

The receptacle according to the present invention for accommodating the analysis chip is shown in FIG. 1 in detail in connection with the example of a receptacle for accommodating an analysis chip for carrying out a DNA analysis, whose analysis result is investigated with the aid of an optical measuring method.

The receptacle shown at the bottom may be used analogously also for chips for the analysis of any type of molecule or biological samples. The measuring method used is moreover not limited to an optical measuring method.

FIG. 1 shows a cross section through housing 10 of a receptacle according to the present invention for accommodating an analysis chip 40. Receptacle housing 10 has a recess 11 adapted to analysis chip 40, in which recess the analysis chip 40 is fastened. Above and below the analysis chip 40, receptacle housing 10 has opening regions 12*a*, 12*b*, respectively, which are laid out as windows for an optical measuring method.

Analysis chip 40 includes two glass plates 41, 42, between which there is a chemically active layer 43. In lower glass plate 42 several channels 44 are formed, which open out on the upper side of glass plate 42 into meanderingly designed channels 45 within chemically active layer 43. On the underside of glass plate 42, each of channels 44 is tightly connected to a channel 20 in receptacle housing 10 by a seal 21, which is designed as a flat seal. Channels 20 perform the function of supply and discharge line for an analysis medium. Alternatively, seal 21 may also be designed as an adhesive.

Figure 2:
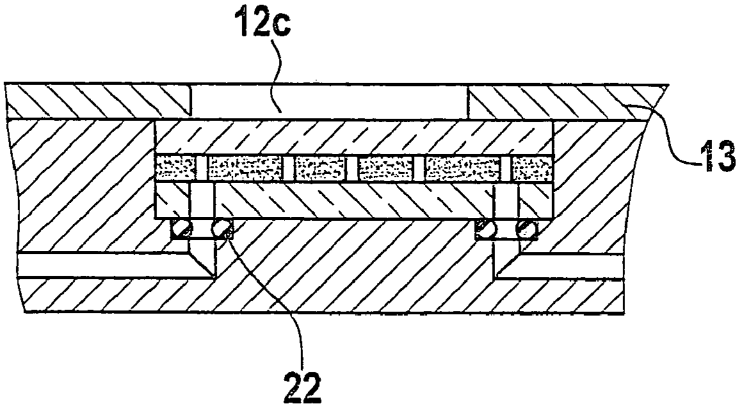
FIG. 2 shows an alternative exemplary embodiment for a mounting support for the accommodation and a seal for the analysis chip in the receptacle according to the present invention.

FIG. 2 shows an additional exemplary embodiment of the present invention, analysis chip 40 being accommodated in housing 10 of the receptacle according to the present invention, analogous to FIG. 1. Each channel 44 of lower glass plate 42 is tightly connected in a lower part to one of channels 20 of receptacle 10, using a ring-shaped sealing element 22. Above analysis chip 40, there is a lid 13, by which analysis chip 40 is pressed against elastic sealing elements 22. Lid 13 establishes a tight connection to receptacle housing 10, which connection may be made as an adhesive or a welding. Above analysis chip 40, lid 13 has an open area 12*c*, which is designed to be a window for an optical measuring method.

Alternatively, lid 13 may also be connected to receptacle housing 10 via a reversible connection, e.g., using a sealing element and a clamping device, this then making possible a multiple utilization of the receptacle.

Figure 3:
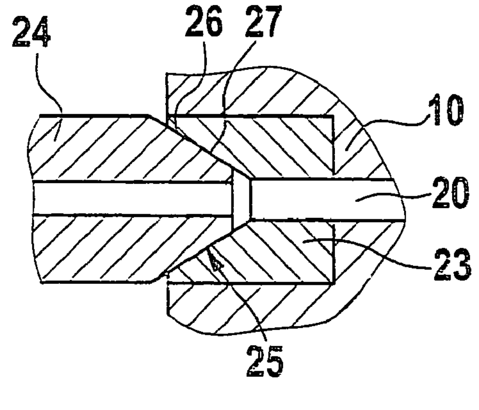
FIG. 3 shows an exemplary embodiment of a connecting arrangement for an external supply line and a discharge line for an analysis medium in the receptacle housing according to the present invention.

FIG. 3 shows an example connecting arrangement for an external supply line or discharge line 24 for the analysis medium, having an opening 25 in receptacle housing 10 according to the present invention, provided for the supply and the discharge of the analysis medium. Channel 20 for the analysis medium opens out in the vicinity of opening 25 into an insertion part 23, which may be made of a metal. Insertion part 23 has a conically formed recess into which a likewise conically formed end section 26 of external supply line and discharge line 24 for the analysis medium penetrates undistortedly in such a way that a tight connection is created over surface 27.

Figure 4:
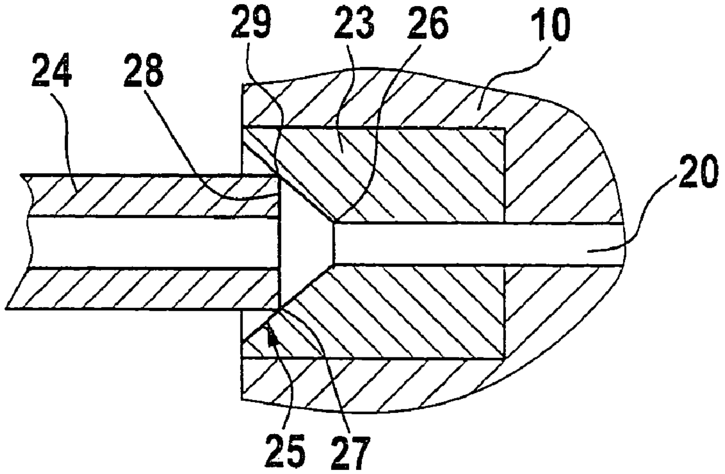
FIG. 4 shows an alternative exemplary embodiment for a connecting arrangement for an external inlet line and discharge line for an analysis medium in the receptacle housing according to the present invention.

FIG. 4 shows an alternative connecting arrangement for external supply line and discharge line 24 for the analysis medium to channel 20 in receptacle housing 10, supply line and discharge line 24 having a planar end section 28 which engages with insertion part 23 in such a way that a sealing of the connection is created by encircling edge 29.

Alternatively, the insertion part may be omitted, so that supply line and discharge line 24 directly rests upon and seals housing 10.

Figure 5:
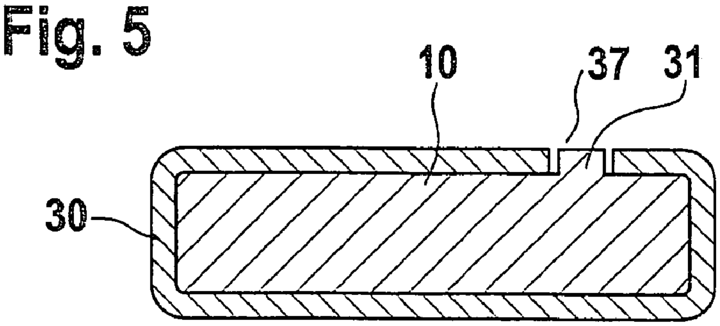
FIG. 5 shows a cross-sectional view of an exemplary embodiment of a housing of the receptacle according to the present invention.

FIG. 5 shows a cross section through housing 10 of the receptacle according to the present invention for analysis chip 40, a movable protector designed as sliding protector 30 being provided, which includes entire housing 10 of the receptacle. Sliding protector 30 has an elongated opening 37 at least on a partial region of its length along its direction of motion, in which a preferably oblong guiding rail 31 engages with receptacle housing 10 undistortedly, so that sliding protector 30 is guided free of swing.

Figure 6:
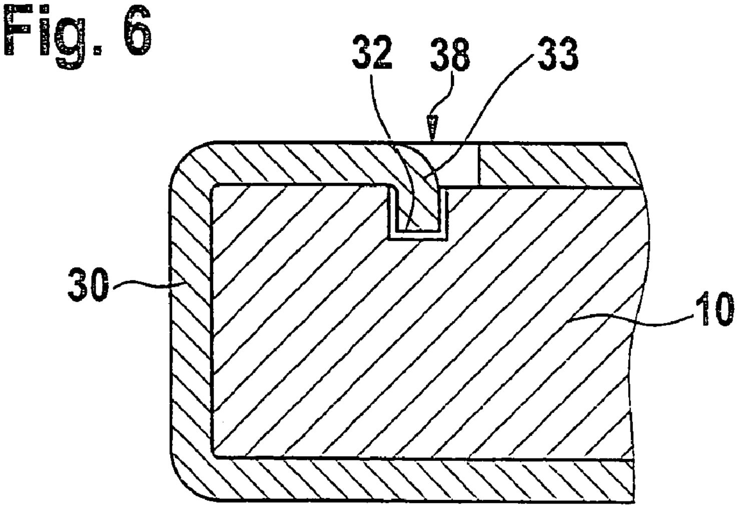
FIG. 6 shows an alternative exemplary embodiment for the guidance of a sliding protector of the receptacle according to the present invention.

FIG. 6 shows an additional example embodiment of the guiding of sliding protector 30 shown in FIG. 5. In this connection, a section of an edge of an opening 38, that extends over at least a partial section of sliding protector 30, forms a bent tab 33 which engages in a guiding groove 32 which extends at least over a partial region of receptacle housing 10, along the direction of motion of sliding protector 30, and which guides sliding protector 30 free of swing during movement.

Alternatively to sliding protector 30, a movable protector designed in a different fashion may be provided on the receptacle, for example, a protector that is connected via a swivel joint to receptacle housing 10 and is movable in a folding down or folding up fashion, or rotatably.

A movable protector designed in accordance with the above characteristics covers, in its closed position, the access to the analysis chip and may be automatically opened by a mechanism within an analysis device. This guarantees a safe handling of the analysis chip outside the analysis device.

In one example embodiment of receptacle housing 10 according to the present invention, a resetting mechanism for sliding protector 30 is provided. As shown in FIG. 7, in this connection, receptacle housing 10, in a separate region 50, has a resetting spring 51, which is fastened in a corner 53 of receptacle housing 10 and a tab 34 of sliding protector 30 which runs in an elongated opening 52 on a narrow side of receptacle housing 10. FIG. 7 shows resetting spring 51 in the closed position of sliding protector 30. In the open position of sliding protector 30, resetting spring 51 is stressed, and exercises a resetting force on sliding protector 30, which independently guides sliding protector 30 back into the closing position again.

FIG. 8 shows a top view onto housing 10 of the receptacle according to the present invention. To provide a clearer understanding, covered analysis chip 40 is illustrated, which is on the inside of receptacle housing 10. Sliding protector 30 has an opening 35*a*, 35*b* on its upper side and its lower side, respectively. Openings 35*a*, 35*b* are applied, in this context, in such a way that opening areas 12*a*, 12*b* in receptacle housing 10, which are located above and below the analysis chip 40, respectively, and are used as windows for an optical measuring method, are closed in the closing position shown in FIG. 8. Sliding protector 30 is able to be guided free of swing into its opening position, from its closing position shown in FIG. 8, along guiding rail 31, opening areas 12*a*, 12*b* being then uncovered in receptacle housing 10 for carrying out an optical measurement through openings 35*a*, 35*b* of sliding protector 30.

In the upper part of FIG. 8, receptacle housing 10 has a coding region 14 which is specified in the exemplary embodiment by five holes and is able to be scanned optically or mechanically. This makes it possible to avoid a mix-up of the analysis chips. In the right upper corner of FIG. 8, a recess 15 on receptacle housing 10 is shown, which clearly defines the latter's spatial orientation in the analysis device.

FIG. 9 shows a lateral view of housing 10 of the receptacle in FIG. 8 according to the present invention, sliding protector 30 having an additional opening 36, which uncovers openings 25 in receptacle housing 10 in the open position of sliding protector 30, which, in the closed position of sliding protector 30 are covered by the latter and are shown, in FIG. 9, only for illustrative purposes. On tab 34 of sliding protector 30, which engages with elongated opening 52 of receptacle housing 10, resetting spring 51 is fastened which, in the open position of sliding protector 30, exercises a resetting force on sliding protector 30, and guides it back to the closed position.

Receptacle housing 10 has a guiding groove 16, which is provided for an opening mechanism that is developed as a pin 65 in a device according to the present invention for accommodating the receptacle, and with which pin 65 engages and guides sliding protector 30 from the closed position into the open position.

FIG. 10 shows a cross section through housing 10 of receptacle 10 according to the present invention as shown in FIGS. 8 and 9, analysis chip 40 being set into recess 11 of receptacle housing 10. Above and below analysis chip 40, receptacle housing 10 has opening regions 12*a*, 12*b*, respectively, which are laid out as windows for an optical measuring method. Sliding protector 30 forms a casing enclosing the entire cross section of receptacle housing 10, whose oblong opening 37 in the right upper part of FIG. 10 lies closely adjacent to guiding rail 31, which is formed as an elevation of receptacle housing 10, so that a swing-free motion of sliding protector 30 is ensured. Openings 25, developed as connections for external supply lines and discharge lines 24 (not shown) are covered by sliding protector 30 in its closed position.

FIG. 11 shows another lateral view of housing 10 of the receptacle according to the present invention shown in FIGS. 8 to 10, having four openings 25 in receptacle housing 10 developed as connections for external supply lines and discharge lines 24 for the analysis medium. For the sake of a better illustration, sliding protector 30 which, corresponding to the embodiment in FIG. 9, covers openings 25 in receptacle housing 10 in its closed position, and uncovers it in its open position, is not shown here.

FIG. 12 shows a cross section through the device according to the present invention for accommodating the receptacle according to the present invention. For this, the device has an opening region 61 in housing 60, which is on the front side of the device. In this opening region 61 an accommodating device, e.g., developed as a drawer 62, is stored, whose accommodating region 64 has a depression that is adapted true to shape to receptacle housing 10, so that the receptacle set into accommodating region 64 has a wobble-free seat. Drawer 62, as shown in FIG. 12, is charged with receptacle housing 10 in an open position. Structural part 63 in drawer 62, which, corresponding to recess 15, is formed on receptacle housing 10, in this context, secures the clear position of receptacle housing 10 within accommodating region 64 of drawer 62.

On the inside of housing 60, there is a mechanism formed as pin 65, which, during the closing procedure of drawer 62, is guided both along a depression 66 in drawer 62 and along guiding groove 16 of receptacle housing 10, and, in this context, carries sliding protector 30 of receptacle housing 10 along with it, so that the sliding protector is brought from the closed position into the open position.

FIG. 13 shows drawer 62 loaded with the receptacle according to the present invention in a closed position, sliding protector 30 of the receptacle having been brought into its open position by firmly installed pin 65 of the device according to the present invention. In this connection, openings 12*a*, 12*b*, developed as windows for an optical measuring method, are uncovered in receptacle housing 10 by openings 35*a*, 35*b* of the sliding protector. In the same way, openings 25, not shown in FIG. 13, in receptacle housing 10, which are developed as connections for the external, and likewise not shown, supply lines and discharge lines 24 for the analysis medium, are uncovered by the sliding protector.

A mechanical scanning device 70, provided for scanning of coding region 14, which is on receptacle housing 10, is positioned above or below coding region 14, and is made up of pins 71, which, with the aid of a mechanism not described in more detail, engages with the holes provided in coding region 14. The position of the pins is evaluated in the usual way, which is not described in greater detail below. Alternatively to scanning coding region 14, an optical scanning device (not shown) may be provided, the scanning device having one or more light sources whose light shines through the holes provided in coding device 14, and is detected by one or more photosensors, and evaluated by an evaluating device that is not described in greater detail.

For this, there may be provided both a scanning device 70 installed on the inside of the device, coding region 14 being supplied only in a closed position of drawer 62 to scanning device 70, and a scanning device 70 installed on drawer 62, the evaluation of coding region 14 already taking place in an open position of drawer 62.

A device designed corresponding to the above exemplary embodiment, for accommodating the receptacle according to the present invention, for carrying out an analysis, ensures a safe and precise applying of the analysis chip to the analysis environment, and consequently makes possible reproducible analysis results along with simplified handling of the analysis chip.

What is claimed is:

1. A receptacle for accommodating an analysis chip, comprising:

a housing having an accommodation region for the analysis chip, the housing also having a first opening with access to the analysis chip for facilitating supply of an analysis medium, and at least one additional opening with access to the analysis chip accommodated in the housing, the at least one additional opening being formed as an open window for facilitating checking the analysis chip with an optical measuring method; and a movable protector, wherein, in a closed position relative to the housing, the movable protector covers the first opening and the at least one additional opening, and wherein, in an open position relative to the housing, the movable protector uncovers the first opening and the at least one additional opening.

2. The receptacle as recited in claim 1, wherein the movable protector is a sliding element that is slidingly moved along a guideway provided on the housing.

3. The receptacle as recited in claim 1, further comprising a seal provided between the housing and the movable protector, wherein the seal is made of a non-woven fabric, and wherein the seal seals at least one of the first opening and the at least one additional opening when the movable protector is in the closed position.

4. The receptacle as recited in claim 1, wherein the analysis chip is for the analysis of DNA.

5. The receptacle as recited in claim 1, wherein a coding region is provided on the housing, the coding region having an array of bores that are adapted to be at least one of optically and mechanically scanned.

6. The receptacle as recited in claim 1, wherein a recess is provided on the housing, the recess establishing the spatial orientation of the receptacle.

7. The receptacle as recited in claim 1, further comprising:

a seal provided between the housing and the movable protector, wherein the seal is made of a non-woven fabric, and wherein the seal seals at least one of the first opening and the at least one additional opening when the movable protector is in the closed position, wherein the movable protector is a sliding element that is slidingly moved along a guideway provided on the housing.

8. The receptacle as recited in claim 1, wherein the analysis chip is for the analysis of DNA, wherein a coding region is provided on the housing, the coding region having an array of bores that are adapted to be at least one of optically and mechanically scanned, and wherein a recess is provided on the housing, the recess establishing the spatial orientation of the receptacle.

9. The receptacle as recited in claim 1, further comprising:

a seal provided between the housing and the movable protector, wherein the seal is made of a non-woven fabric, and wherein the seal seals at least one of the first opening and the at least one additional opening when the movable protector is in the closed position, wherein the movable protector is a sliding element that is slidingly moved along a guideway provided on the housing, wherein the analysis chip is for the analysis of DNA, wherein a coding region is provided on the housing, the coding region having an array of bores that are adapted to be at least one of optically and mechanically scanned, and wherein a recess is provided on the housing, the recess establishing the spatial orientation of the receptacle.

10. The receptacle as recited in claim 9, wherein the analysis chip is in the housing, wherein the analysis chip includes an upper glass plate and lower glass plate between which there is a chemically active layer, wherein the lower glass plate has at least two channels, which open out on an upper side of the lower glass plate into channels within the chemically active layer, and wherein on an underside of the lower glass plate, each of the channels is connected to a channel in the housing by the seal.

11. The receptacle as recited in claim 1, wherein the analysis chip is in the housing, wherein the analysis chip includes an upper glass plate and lower glass plate between which there is a chemically active layer, wherein the lower glass plate has at least two channels, which open out on an upper side of the lower glass plate into channels within the chemically active layer, and wherein on an underside of the lower glass plate, each of the channels is connected to a channel in the housing by the seal.

* * * * *

UNITED STATES PATENT AND TRADEMARK OFFICE
CERTIFICATE OF CORRECTION

PATENT NO. : 7,585,662 B2
APPLICATION NO. : 10/477160
DATED : September 8, 2009
INVENTOR(S) : Weiblen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1075 days.

Signed and Sealed this

Fourteenth Day of September, 2010

David J. Kappos
*Director of the United States Patent and Trademark Office*